(12) United States Patent
Kumar et al.

(10) Patent No.: US 7,649,096 B2
(45) Date of Patent: Jan. 19, 2010

(54) PROCESS FOR THE PREPARATION OF A CRYSTALLINE FORM OF (S)-N [[3-(3-FLUORO-4(4-MORPHOLINYL) PHENYL]-2-OXO-5-OXAZOLIDINYL] METHYL] ACETAMIDE

(75) Inventors: Bobba Venkata Siva Kumar, Navi Mumbai (IN); Pravin Bhalchandra Kulkarni, Kalyan (IN); Girish Bansilal Patel, Navi Mumbai (IN); Nitin Sharad Chandra Pradhan, Thane (IN)

(73) Assignee: Glenmark Pharmaceuticals Limited, Mumbai (IN)

( * ) Notice: Subject to any disclaimer, the term of this patent is extended or adjusted under 35 U.S.C. 154(b) by 381 days.

(21) Appl. No.: 11/487,766

(22) Filed: Jul. 17, 2006

(65) Prior Publication Data
US 2007/0015753 A1    Jan. 18, 2007

(30) Foreign Application Priority Data
Jul. 15, 2005    (IN) .................................. 853/2005

(51) Int. Cl.
C07D 413/10    (2006.01)
C07D 413/02    (2006.01)

(52) U.S. Cl. ..................................................... 548/137

(58) Field of Classification Search .................. 544/137
See application file for complete search history.

(56) References Cited

U.S. PATENT DOCUMENTS

| 5,688,792 A | 11/1997 | Barbachyn et al. |
| 6,444,813 B2 | 9/2002 | Bergren et al. |
| 6,559,305 B1 | 5/2003 | Bergren et al. |

OTHER PUBLICATIONS

Morissette et al. Advanced Drug Delivery Reviews 2004, 56, 275-300.*
Thayer, A.M. Chemical & Engineering News, Jul. 18, 2007, 85(25), 17-30.*
Rouhi, A. M. Chem. & Eng. News, 2003.*

* cited by examiner

*Primary Examiner*—Rebecca L Anderson
*Assistant Examiner*—Jason Nolan
(74) *Attorney, Agent, or Firm*—M. Carmen & Associates, PLLC

(57) ABSTRACT

A process for preparing a crystalline form of linezolid is provided comprising (a) providing a solution comprising linezolid in an organic solvent having a boiling point of less than or equal to about 150° C.; (b) adding an anti-solvent having a boiling point greater than or equal to about 50° C. to the solution; and (c) recovering the crystalline form of linezolid.

9 Claims, 2 Drawing Sheets

PROCESS FOR THE PREPARATION OF A CRYSTALLINE FORM OF (S)-N [[3-(3-FLUORO-4(4-MORPHOLINYL) PHENYL]-2-OXO-5-OXAZOLIDINYL] METHYL] ACETAMIDE

PRIORITY

This application claims the benefit under 35 U.S.C. §119 to Indian Provisional Application 853/MUM/2005, filed on Jul. 15, 2005, and entitled "PROCESS FOR THE PREPARATION OF (S)-N[[3-(3-FLUORO-4-(4-MORPHOLINYL) PHENYL]-2-OXO-5-OXAZOLIDINYL]METHYL]ACETAMIDE", the contents of which are incorporated by reference herein.

BACKGROUND OF THE INVENTION

1. Technical Field

The present invention generally relates to a process for preparing a crystalline form of (S)-N[[3-(3-fluoro-4-(4-morpholinyl)phenyl]-2-oxo-5-oxazolidinyl]methyl]acetamide.

2. Description of the Related Art

Linezolid, also known as (S)-N-[[3-[3-fluoro-4-(4-morpholinyl)phenyl]-2-oxo-5-oxazolidinyl]methyl]acetamide, can be represented by the structure of general Formula I.

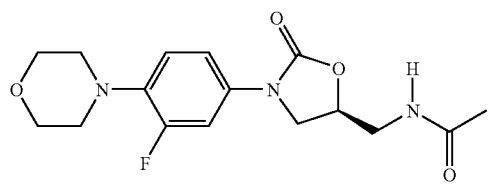

(I)

Linezolid is a synthetic antibacterial agent of the oxazolidinone class. Linezolid has clinical utility in the treatment of infections caused by aerobic Gram-positive bacteria. The in vitro spectrum of activity of linezolid also includes certain Gram-negative bacteria and anaerobic bacteria. Linezolid inhibits bacterial protein synthesis through a mechanism of action different from that of other antibacterial agents, therefore, cross-resistance between linezolid and other classes of antibiotics is unlikely. Linezolid binds to a site on the bacterial 23S ribosomal RNA of the 50S subunit and prevents the formation of a functional 70S initiation complex, which is an essential component of the bacterial translation process. The results of time-kill studies have shown linezolid to be bacteriostatic against enterococci and staphylococci. For streptococci, linezolid was found to be bactericidal for the majority of strains. Linezolid is commercially sold under the trade name Zyvox®. See, e.g., The Merck Index, Thirteenth Edition, 2001, p. 986-87, monograph 5526; and Physician's Desk Reference, "Zyvox," 58th Edition, pp. 2808-2815 (2004).

U.S. Pat. No. 5,688,792 discloses linezolid and a process for its preparation.

U.S. Pat. Nos. 6,444,813 and 6,559,305 ("the '305 patent") disclose crystal Form II of linezolid. The '305 patent further discloses that crystal Form II of linezolid has a powder X-ray diffraction spectrum of characteristic peaks (expressed in degrees 2θ±0.2° θ) at 7.10, 9.54, 13.88, 14.23, 16.18, 16.79, 17.69, 19.41, 19.69, 19.93, 21.61, 22.39, 22.84, 23.52, 24.16, 25.28, 26.66, 27.01 and 27.77 and an infrared (IR) spectrum as a mineral oil mull: 3364, 1748, 1675, 1537, 1517, 1445, 1410, 1401, 1358, 1329, 1287, 1274, 1253, 1237, 1221, 1145, 1130, 1123, 1116, 1078, 1066, 1049, 907, 852 and 758 cm$^{-1}$.

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. Additionally, polymorphic forms of the same drug substance or active pharmaceutical ingredient, can be administered by itself or formulated as a drug product (also known as the final or finished dosage form), and are well known in the pharmaceutical art to affect, for example, the solubility, stability, flowability, tractability and compressibility of drug substances and the safety and efficacy of drug products. Therefore, there is a continuing need for new crystalline forms and new processes of preparing crystalline forms.

SUMMARY OF THE INVENTION

In accordance with one embodiment of the present invention, a process for preparing a crystalline form of linezolid is provided comprising (a) providing a solution comprising linezolid in an organic solvent having a boiling point of less than or equal to about 150° C.; (b) adding an anti-solvent having a boiling point greater than or equal to about 50° C. to the solution; and (c) recovering the crystalline form of linezolid.

In accordance with a second embodiment of the present invention, a crystalline form of linezolid prepared by a process comprising (a) providing a solution comprising linezolid in an organic solvent having a boiling point of less than or equal to about 150° C.; (b) adding an anti-solvent having a boiling point greater than or equal to about 50° C. to the solution; and (c) recovering the crystalline form of linezolid is provided.

In accordance with a third embodiment of the present invention, linezolid having a powder x-ray diffraction (XRD) pattern substantially in accordance with FIG. 1 is provided.

In accordance with a fourth embodiment of the present invention, linezolid having a XRD pattern substantially in accordance with FIG. 1 and/or an infrared (IR) spectrum substantially in accordance with FIG. 2 is provided.

In accordance with a fifth embodiment of the present invention, a pharmaceutical composition is provided comprising a therapeutically effective amount of a crystalline form of linezolid prepared by a process comprising (a) providing a solution comprising linezolid in an organic solvent having a boiling point of less than or equal to about 150° C.; (b) adding an anti-solvent having a boiling point greater than or equal to about 50° C. to the solution; and (c) recovering the crystalline form of linezolid, and one or more pharmaceutically acceptable excipients.

In accordance with a sixth embodiment of the present invention, a pharmaceutical composition is provided comprising a therapeutically effective amount of linezolid having a XRD pattern substantially in accordance with FIG. 1 and/or an IR spectrum substantially in accordance with FIG. 2 prepared by a process comprising (a) providing a solution comprising linezolid in an organic solvent having a boiling point of less than or equal to about 150° C.; (b) adding an anti-solvent having a boiling point greater than or equal to about 50° C. to the solution; and (c) recovering the linezolid.

In accordance with a seventh embodiment of the present invention, a pharmaceutical composition is provided comprising a therapeutically effective amount of linezolid having a XRD pattern substantially in accordance with FIG. 1.

DEFINITIONS

The term "treating" or "treatment" of a state, disorder or condition as used herein means: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statistically significant or at least perceptible to the patient or to the physician.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dehydrate and other such material known to those of ordinary skill in the art.

The term "sweetening agent" as used herein is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in tablet granulations. Such compounds include, by way of example and without limitation, acacia alginic acid, tragacanth, carboxymethylcellulose sodium, poly (vinylpyrrolidone), compressible sugar (e.g., NuTab), ethylcellulose, gelatin, liquid glucose, methylcellulose, povidone and pregelatinized starch, combinations thereof and other material known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC™ F68, PLURONIC™ F127), collagen, albumin, celluloses in nonaqueous solvents, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art.

The term "diluent" or "filler" as used herein is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein is intended to mean substances used in tablet formulations to reduce friction during tablet compression. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecyl sulfate, carboxymethylcellulose calcium, carboxymethylcellulose sodium, methylcellulose, hydroxyethylcellulose, hydroxylpropylcellulose, hydroxypropylmethylcellulose phthalate, noncrystalline cellulose, magnesium aluminum silicate, triethanolamine, polyvinyl alcohol, and polyvinylpyrrolidone (PVP). Tyloxapol (a nonionic liquid polymer of the alkyl aryl polyether alcohol type, also known as superinone or triton) is another useful wetting agent, combinations thereof and other such materials known to those of ordinary skill in the art.

Most of these excipients are described in detail in, e.g., Howard C. Ansel et al., Pharmaceutical Dosage Forms and Drug Delivery Systems, (7th Ed. 1999); Alfonso R. Gennaro et al., Remington: The Science and Practice of Pharmacy,

DETAILED DESCRIPTION OF THE PREFERRED EMBODIMENTS

The present invention is directed to a process for preparing a crystalline form of linezolid. In one embodiment, a process for preparing a crystalline form of linezolid includes at least (a) providing a solution comprising linezolid in an organic solvent having a boiling point of less than or equal to about 150° C.; (b) adding an anti-solvent having a boiling point greater than or equal to about 50° C. to the solution; and (c) recovering the crystalline form of linezolid.

In step (a) of the process of the present invention, a solution is prepared containing at least linezolid in an organic solvent having a boiling point of less than or equal to about 150° C. Linezolid is well known and can be obtained by any known technique. See, e.g., U.S. Pat. Nos. 5,688,792; 6,444,813 and 6,559,305; the contents of each of which are incorporated by reference herein. Suitable organic solvents for use herein include those having a boiling point less than or equal to about 150° C., and preferably less than or equal to about 100° C. Useful solvents include, but are not limited to, chlorinated solvents, e.g., methylene chloride, ethylene chloride, chloroform, and the like; alcoholic solvents, e.g., methanol, ethanol, isopropanol and the like; aliphatic or cyclic ethers, e.g., tetrahydrofuran, monoglyme and the like and mixtures thereof.

In step (b) of the process of the present invention, an anti-solvent having a boiling point greater than or equal to about 50° C. is added to the solution. Suitable anti-solvents for use herein include those having a boiling point greater than or equal to about 50° C. and preferably greater than or equal to about 100° C. Representative examples of such anti-solvents include, but are not limited to, o-xylene, m-xylene, p-xylene, mesitylene, diphenyl ether, n-heptane and the like and mixture thereof. Preferably, the anti-solvent is o-xylene, m-xylene, p-xylene and mixture thereof.

Figure 1:
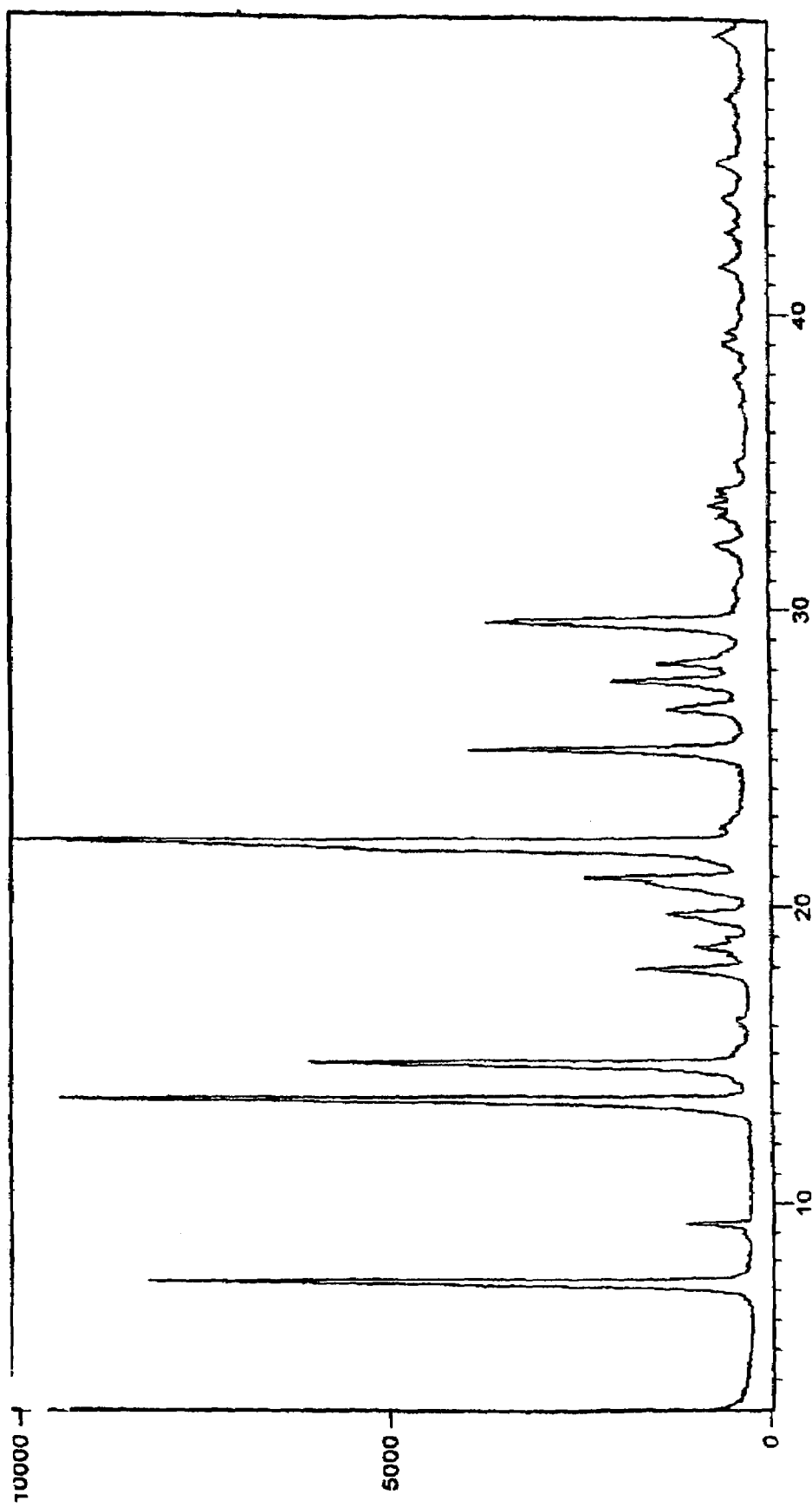
FIG. 1 is a characteristic powder x-ray diffraction pattern of linezolid of the present invention.
Figure 2:
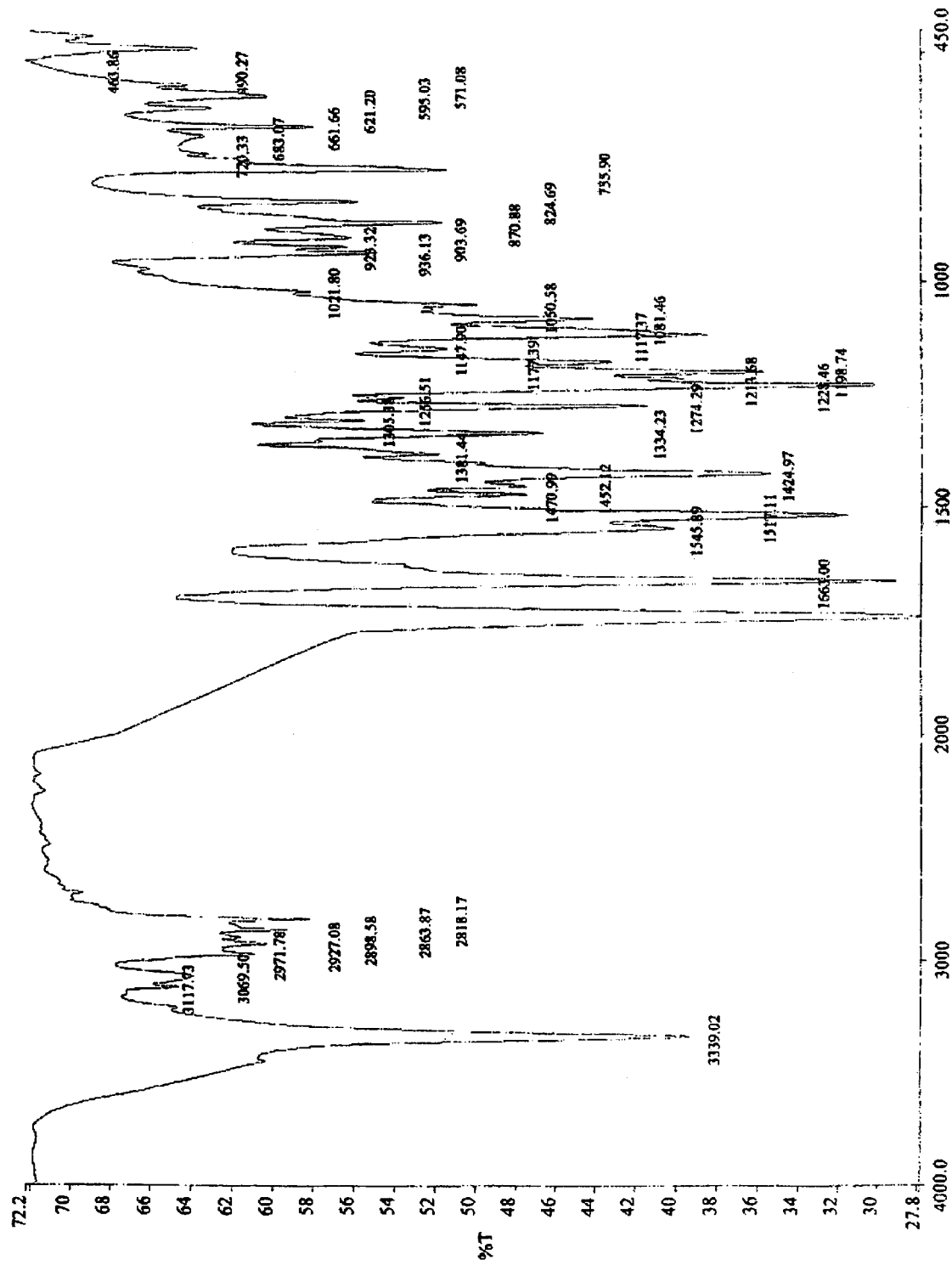
FIG. 2 is a characteristic infra red spectrum of linezolid of the present invention.

Following the addition of the anti-solvent to the solution, the organic solvent is removed, e.g., either by evaporating in a rotatory evaporator or under stirring. The organic solvent can be removed at a temperature ranging from about 30° C. to about 120° C., preferably from about 50° C. to about 80° C. and more preferably from about 60° C. to about 70° C. Next, a crystalline form of linezolid is isolated by known techniques, e.g., filtration. The crystalline form of linezolid thus obtained can be characterized by a powder x-ray diffraction (XRD) pattern substantially in accordance with FIG. 1 and/or an IR spectrum substantially in accordance with FIG. 2.

Another aspect of the present invention is directed to pharmaceutical compositions containing at least the linezolid prepared in accordance with the present invention. Such pharmaceutical compositions may be administered to a mammalian patient in any dosage form, e.g., liquid, powder, elixir, injectable solution, etc. Dosage forms may be adapted for administration to the patient by oral, buccal, parenteral, ophthalmic, rectal and transdermal routes. Oral dosage forms include, but are not limited to, tablets, pills, capsules, troches, sachets, suspensions, powders, lozenges, elixirs and the like.

The linezolid of the present invention also may be administered as suppositories, ophthalmic ointments and suspensions, and parenteral suspensions, which are administered by other routes. The dosage forms may contain the linezolid of the present invention as is or, alternatively, may contain the linezolid of the present invention as part of a composition. The pharmaceutical compositions may further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinabove.

Capsule dosages can contain the linezolid of the present invention within a capsule which may be coated with gelatin. Tablets and powders may also be coated with an enteric coating. The enteric-coated powder forms may have coatings comprising phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

Tableting compositions may have few or many components depending upon the tableting method used, the release rate desired and other factors. For example, the compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

In one embodiment, the linezolid of the present invention for use in the pharmaceutical compositions of the present invention can have a $D_{50}$ and $D_{90}$ particle size of less than about 400 microns, preferably less than about 200 microns, more preferably less than about 150 microns, still more preferably less than about 50 microns and most preferably less than about 15 microns. The particle sizes of the linezolid of the present invention can be obtained by, for example, any milling, grinding, micronizing or other particle size reduction method known in the art to bring the solid state the linezolid of the present invention into any of the foregoing desired particle size range.

Actual dosage levels of the linezolid of the present invention may be varied to obtain an amount of the linezolid of the present invention that is effective to obtain a desired therapeutic response for a particular composition and method of administration for treatment of a mammal. The selected dosage level therefore depends upon such factors as, for example, the desired therapeutic effect, the route of administration, the desired duration of treatment, and other factors. The total daily dose of the linezolid of the present invention administered to a host in single or divided dose and can vary widely depending upon a variety of factors including, for example, the body weight, general health, sex, diet, time and route of administration, rates of absorption and excretion, combination with other drugs, the severity of the particular condition being treated, etc.

The following examples are provided to enable one skilled in the art to practice the invention and are merely illustrative of the invention. The examples should not be read as limiting the scope of the invention as defined in the features and advantages.

Example 1

Preparation of Crystalline Form of Linezolid

A 1 liter distillation flask was charged with a solution of linezolid in methylene chloride (30 grams in 300 ml)) and o-xylene as an anti-solvent was added and stirred for 20 to 25 minutes. Methylene chloride was distilled out of the solution in a rotatory evaporator at a bath temperature of 60° C. to 70° C. During distillation solids began to precipitate out. After completion of the distillation, the precipitated solids were isolated by filtration and dried to provide linezolid (25 g, 83%) having a characteristic x ray powder diffraction pattern and infra red spectra substantially in accordance with FIGS. 1 and 2, respectively.

Example 2

Preparation of Crystalline Form of Linezolid

A 1 liter distillation flask was charged with a solution of linezolid (30 g) in methylene chloride (150 ml) and tetrahydrofuran (300 ml) and o-xylene (120 ml) as an anti-solvent was added and stirred for 20 to 25 minutes. Methylene chloride and tetrahydrofuran were distilled out of the solution in a rotatory evaporator by raising the bath temperature up to 120° C. During distillation, solids began to precipitate out. After completion of the distillation, the precipitated solids were isolated by filtration and dried to provide linezolid (23 g, 76.6%) having a characteristic x ray powder diffraction pattern and infra red spectra substantially in accordance with FIGS. 1 and 2, respectively.

While the above description contains many specifics, these specifics should not be construed as limitations of the invention, but merely as exemplifications of preferred embodiments thereof. Those skilled in the art will envision many other embodiments within the scope and spirit of the invention as defined by the features and advantages appended hereto.

What is claimed is:

1. A process for preparing a crystalline form of linezolid comprising (a) providing a solution comprising linezolid in an organic solvent wherein the organic solvent is selected from the group consisting of a chlorinated solvent, alcoholic solvent, aliphatic or cyclic ether and mixtures thereof; (b) adding an anti-solvent, wherein the anti-solvent is selected from the group consisting of o-xylene, m-xylene, p-xylene, mesitylene, diphenyl ether, n-heptane and mixture thereof to the solution; and (c) recovering the crystalline form of linezolid; wherein the crystalline form of linezolid is characterized by a powder x-ray diffraction (XRD) pattern substantially in accordance with FIG. 1 and/or an infra red (IR) spectrum substantially in accordance with FIG. 2.

2. The process of claim 1, wherein the chlorinated solvent is selected from the group consisting of methylene chloride, ethylene chloride, chloroform, and the mixtures thereof.

3. The process of claim 1, wherein the alcoholic solvent is selected from the group consisting of methanol, ethanol, isopropanol and mixtures thereof.

4. The process of claim 1, wherein the aliphatic or cyclic ether solvent is selected from the group consisting of tetrahydrofuran, monoglyme and mixtures thereof.

5. The process of claim 1, wherein step (c) comprises removing the organic solvent.

6. The process of claim 5, wherein the organic solvent is removed by evaporation in a rotatory evaporator or under stirring at a temperature of about 30° C. to about 120° C.

7. The process of claim 5, wherein the organic solvent is removed by evaporation at a temperature of about 50° C. to about 80° C.

8. The process of claim 5, wherein the organic solvent is removed by evaporation at a temperature of about 60° C. to about 70° C.

9. The process of claim 5, further comprising filtering the crystalline form of linezolid.

* * * * *